United States Patent [19]

Kalmakis et al.

[11] Patent Number: 4,896,270

[45] Date of Patent: Jan. 23, 1990

[54] COMPUTER CONTROLLED PIPETTING SYSTEM

[75] Inventors: George P. Kalmakis, Reading; R. Laurence Keene, Brookline, both of Mass.; Gary E. Nelson, Nashua, N.H.; Victor A. Torti, Groton, Mass.

[73] Assignee: Matrix Technologies Corporation, Lowell, Mass.

[21] Appl. No.: 842,629

[22] Filed: Mar. 21, 1986

[51] Int. Cl.4 .......................... G06F 15/42; G01N 1/14
[52] U.S. Cl. .................................. 364/479; 73/864.16; 364/497; 364/571; 422/100
[58] Field of Search ............... 364/479, 500, 496, 497, 364/571; 422/62, 81, 100; 73/864.01, 864.11–864.18, 864.24, 864.25, 863.01; 222/420

[56] References Cited

U.S. PATENT DOCUMENTS 4,399,712  8/1983  Oshikubo et al. ............... 422/100 X
4,422,151  12/1983  Gilson .................................. 364/496
4,567,780  2/1986  Oppenlander et al. .......... 73/864.16
4,593,837  6/1986  Jakubowicz et al. ......... 73/864.17 X
4,633,413  12/1986  Caveney et al. ............. 73/864.12 X Primary Examiner—Joseph Ruggiero
Attorney, Agent, or Firm—Jerry Cohen

[57] ABSTRACT

A computer controlled pipetting system with a hand held pipettor and a control assembly. The pipettor has a motor driven pump for aspirating and dispensing liquid through a pipette which is inserted to the pipettor. The control assembly has a keyboard for controlling operation of the pipetting system. A calibration pipette is inserted into the pipettor for establishing reference signals corresponding to a selected density and temperature of a liquid which is aspirated into the calibration pipette by the pump. The reference signals are stored in a memory and subsequently used for aspirating selected quantities of liquid into a laboratory pipette which is inserted into the pipettor in place of the calibration pipette.

2 Claims, 2 Drawing Sheets

COMPUTER CONTROLLED PIPETTING SYSTEM

BACKGROUND OF THE INVENTION

1. Field of the Invention

The present invention relates to liquid transfer devices used in laboratories and, more particularly, is directed toward electronic pipetting devices.

2. Description of the Prior Art

Pipettes are precision glass or plastic tubes which are used in laboratories for the transfer of relatively small quantities of liquids, for example quantity to 100 ml, typically 0.01 ml to 50 ml, and specifically 0.1 to 30 ml. The pipette is used by placing it into a reservoir (flask, beaker, etc.) of liquid and creating suction via a mechanical device or one's mouth to draw liquid into the pipette. The mouth piece portion of the pipette is fitted with a cotton plug to protect the user from ingesting dangerous liquids or to prevent contamination of the mechanical system. By visually monitoring the level of liquid in the pipette accordingly to graduations printed thereon, the user is able to match the amount of liquid to the desired volume. Currently designed manual and electronic pipetting systems suffer from the disadvantage that the filling of pipettes to a precise level is a time consuming and tedious task. In addition, errors are caused by user inconsistencies. Furthermore, since a new pipette is often used for each liquid sample, precision made plastic or glass pipettes, which are costly to manufacture, are necessary to maintain consistency between pipettes. Current air displacement systems are calibrated to water at 20° C. as the standard. A need exists for a method of pipetting liquids with various densities and at different temperatures accurately using air displacement. Also, a need exists for improvements in pipette systems and associated pipettes.

SUMMARY OF THE INVENTION

It is an object of the present invention to provide an electronic pipette system which does no suffer from the heretofore mentioned disadvantages.

It is another object of the invention to provide an electronic pipetting system which rapidly and precisely aspirates and dispenses liquid based upon a predetermined reference.

It is a further object of the invention to provide a computer controlled pipetting system with a hand held pipettor and a control assembly. The pipettor has a motor driven pump with a piston that reciprocates within a cylinder for aspirating and dispensing a liquid into and from a pipette removably attached to the pipettor. The control assembly has a keyboard and associated circuits for controlling operation of the pipetting system. A trigger on the pipettor actuates the pump for aspirating and dispensing liquid. Calibration data signals, which define the distance that the piston has moved from a home position within the cylinder to an away position in order to aspirate a selected quantity of liquid into a calibration pipette attached to the pipettor, are stored in a calibration memory. These stored calibration data signals are used during normal operation of the pipetting system to aspirate and dispense the selected quantity of liquid into and from a laboratory pipette which is attached to the pipettor in place of the calibrated pipette. A keyboard on the control assembly is provided for controlling the operation of the system.

The calibration pipette is a precision pipette which is used to calibrate the pipetting system for a liquid of specific density and temperature. Once the system has been calibrated, the calibration pipette is removed and replaced with a less costly laboratory pipette.

The invention accordingly comprises the methods and apparatuses, together with their steps, parts, elements and interrelationships, that are ex-emplified in the following disclosure, the scope of which will be indicated in the appended claims.

BRIEF DESCRIPTION OF THE DRAWINGS

A fuller understanding of the nature and objects of the present invention will become apparent upon consideration of the following detailed description taken in connection with the accompanying drawings, wherein.

DETAILED DESCRIPTION OF THE PREFERRED EMBODIMENTS

Figure 1:
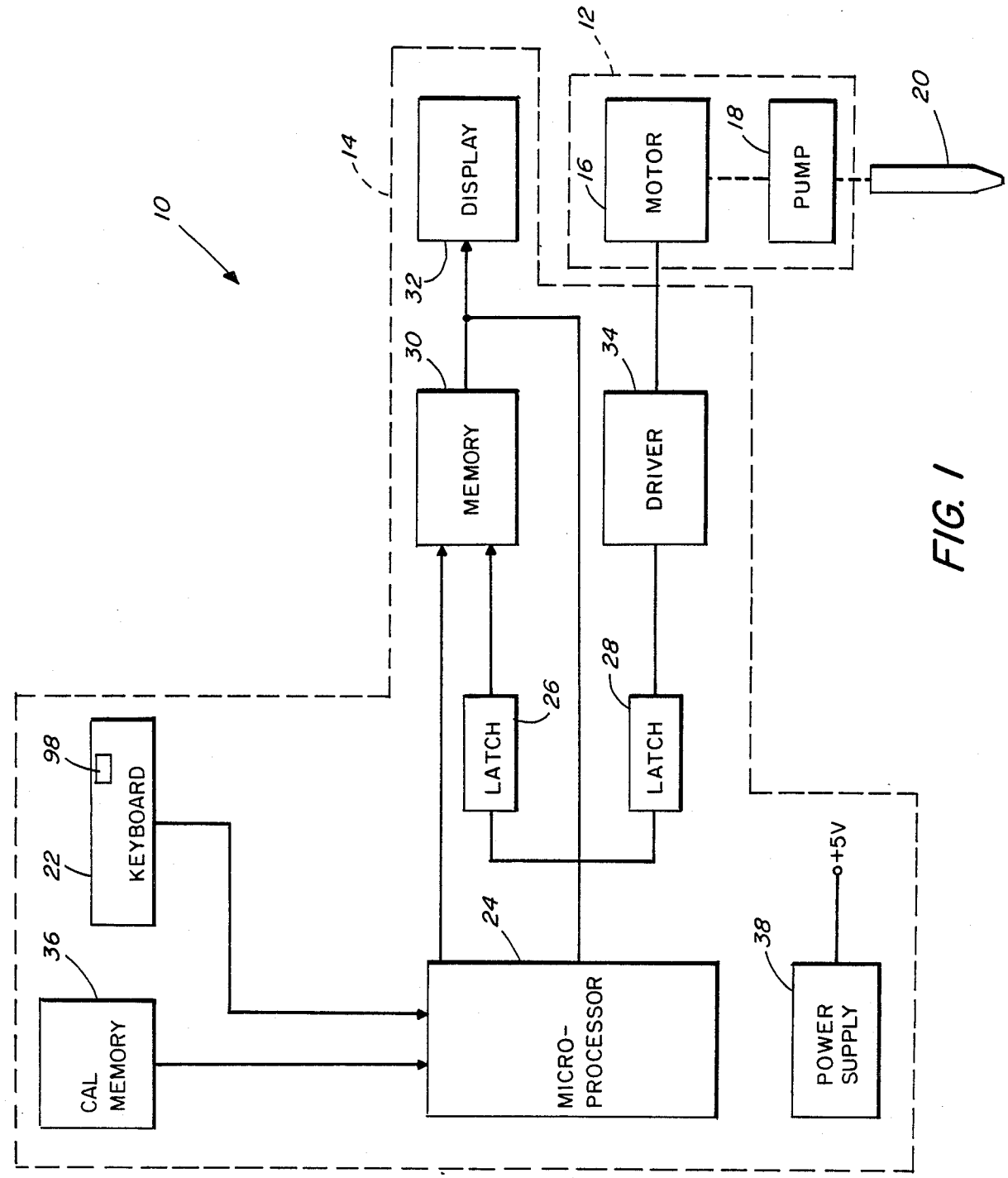
FIG. 1 is a block and schematic diagram of a pipetting system embodying the present invention.
Figure 2:
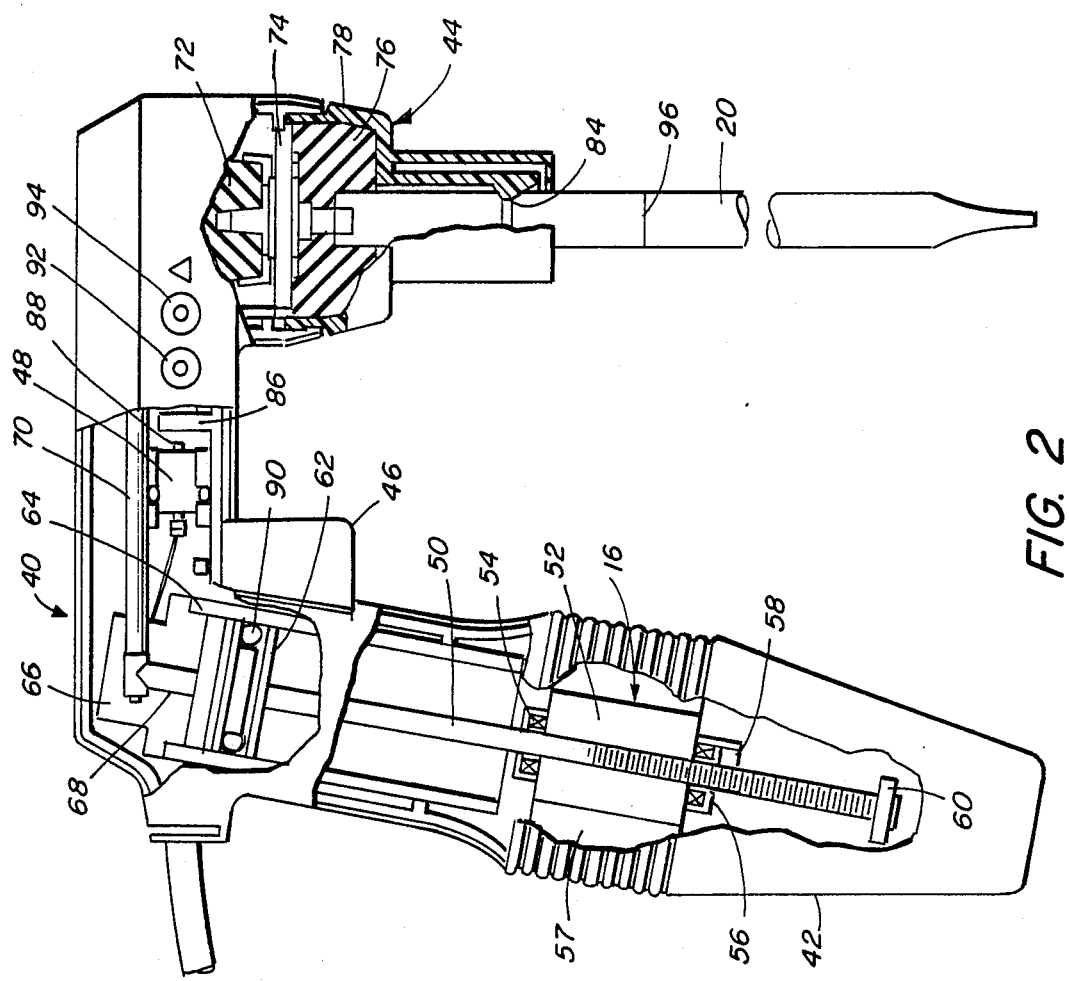
FIG. 2 is a side view, partly broken-away, of a pipettor made according to the present invention.

Referring now to the drawings, particularly FIG. 1, there is shown a pipetting system 10 made in accordance with the present invention. Pipetting system 10 includes a hand held pipettor 12, the details of which are shown in FIG. 2, and a control assembly 14. Pipettor 12 has a motor 16, for example a stepping motor, which drives a pump assembly 18 for aspirating and dispensing liquid into and from a pipette 20 which is removably attached to the pipettor. Control assembly 14 includes a keyboard 22 which is connected to a micro-processor 24. Keyboard 22 provides an operator with the ability of manually inputting micro-processor 24. Data signals generated from micro-processor 24 are applied to latches 26 and 28, as well as a memory 30. Latch 26 and memory 30 are used in conjunction with a display 32 for indicating the status of pipetting system 10. Latch 28 is used in connection with motor 16. The signals at the output of latch 28 are applied to a driver 34 which generates drive signals for controlling motor 16. A calibration memory unit 36 is provided for storing calibration data signals for use in pipetting system 10 as hereinafter described. A power supply 38 generates a 5 volt signal, for example, which is applied to the electronic circuits hereinbefore. The detail construction of pipettor 12 is shown in FIG. 2.

Pipettor 12 includes a casing 40 having a handle 42 at one end and a pipette receiving receptacle 44 at the other end. A trigger 46 is slidably mounted to casing 40 and engages a switch 48 when the trigger is actuated. Switch 48 energizes motor 16 whereupon a shaft 50 moves upwardly and downwardly relative to motor 16 in response to rotation of the motor armature 52. The motor 16 is mounted to handle 42 in a pair of bearings 54, 56, the motor housing and stator 57 being constrained against movement relative to the handle. In the illustrated embodiment, shaft 50 is externally threaded and armature 52 is an internally threaded member. Accordingly, clockwise and counterclockwise rotational movement of armature 52 produces upward and downward linear movement of shaft 50. When armature 52 rotates in a clockwise direction shaft 50 moves up, for example, and when the armature rotates in a counterclockwise motion the shaft moves down.

A sensor 58 is positioned adjacent bearing 56 and senses the relative position of shaft 50. In the illustrated embodiment, by way of example, sensor 58 is a' Hall effect sensor and a magnet 60 is mounted to the lower end of shaft 50. The Hall effect sensor 58 generates signals which define the position of magnet 60 relative to the sensor. A piston 62, which is constrained for reciprocating movement within a cylinder 64, is attached to the upper end of shaft 50. The upper end of cylinder 64 is sealed with a cap 66 having an internal passage 68 which is configured to sealably receive one end of a tube 70. The other end of tube 70 is received in an adaptor 72 which is composed of rubber, for example. One end of a filter 74, for example a sterilizing grade filter, is held in adaptor 72 in communication with tube 70. The other end of filter 74 is received in a filter retainer 76 which is composed of rubber, for example. Pipette receiving receptacle 44 captively fits about retainer 76.

Figure 3:
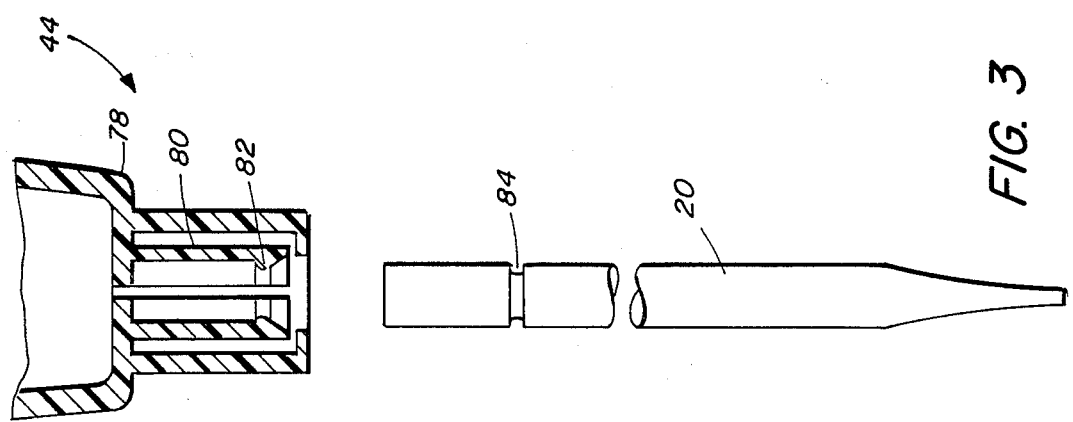
FIG. 3 is a side view of the pipette receptacle of FIG. 2.

As shown in FIG. 3, receptacle 44 has an outer housing 78 and a plurality of downwardly extending fingers 80, for example three fingers, which are radially disposed. The lower section of each finger 80 a projecting gripping member 82 which is configured to engage a pipette inserted into receptacle 44. In the embodiment shown in FIGS. 2 and 3, gripping members 82 are configured to engage an annular recess or constriction portion of a pipette 20 which is inserted into receptacle 44. In an alternative embodiment, not shown, the pipette has an annular ribbed portion which is engaged by gripping members 82. In a further embodiment, the pipette has a smooth outer surface. When pipette 20 is inserted into receptacle 44, gripping members 82 lock onto ribbed portion 84. When the pipette 20 is locked into position, the upper end of the pipette communicates with and is seated in filter retainer 76, the upper end of the pipette being frictionally engaged by the filter retainer.

The operation of pipettor 12 is initiated by actuation of trigger 46. When trigger 46 is squeezed, an actuating arm 86 depresses a contact 88 in switch 48. Switch 48 is actuated and motor 16 is energized. Armature 52 of motor 16 rotates, thereby causing either upward or downward linear movement of shaft 50 relative to the fixed position of motor 16. Piston 62, which is mounted on the end of shaft 50 in sealing engagement with the walls of cylinder 64 by means of an "O" ring 90, moves upwardly and downwardly with movement of the shaft. When piston 62 moves downwardly in cylinder 64, a suction is created in tube 70, whereby liquid is aspirated into pipette 20 which is attached to filter 74. When piston 62 moves upwardly in cylinder 64, pressure is applied to tube 70 and liquid is dispensed from pipette 20. An indicator 92, for example a light emitting diode, provides an indication that liquid is being dispensed from pipette 20 and an indicator 94, for example a light emitting diode, provides an indication that liquid is being drawn into pipette 20. In the illustrated embodiment, by way of example, indicator 92 is a red light emitting diode and indicator 94 is a green light emitting diode.

Sensor 58 provides an indication of the relative position of piston 62 in cylinder 64 by generating signals defining the position of magnet 60 with respect to the sensor. An initial or home position of magnet 60 relative to sensor 58 is the position where filling of pipette 20 begins and equates to zero volume in the pipette.

Pipetting system 10 is calibrated by means of a high precision pipette which is inserted into receptacle 44. The purpose of the calibration process is to calibrate the pipetting system for a liquid of a specific density and at a specific temperature. The calibration procedure begins with the squeezing of trigger 46 and the energizing of motor 16. The liquid is aspirated into the precision calibrated pipette 20 until the liquid level reaches a graduation mark 96 on the calibration pipette. It is preferred that the liquid used during the calibration process has the same density and it is at the same temperature as the liquid which is to be used during normal operation of the pipetting system. Once the desired quantity of liquid has been aspirated into pipette 20, a calibration button 98 on keyboard 22 is pressed and calibration data signals generated in micro-processor 24 are stored in calibration memory 36. The calibration data signals stores the number of steps motor 16 moved to displace the liquid in pipette 20 to the graduation mark. In one example, the graduation line on the calibration pipette represents 10 ml. The calibration of the instrument for each liquid is accomplished by using the calibration data at 10 ml and normalizing the values over the volume range of the instrument, for example 0-12 ml. In the illustrated embodiment, calibration memory 36 is capable of storing five separate calibration data signals. Once the pipetting system 10 has been calibrated, the precision calibration pipette is removed and a laboratory pipette is inserted in its place.

In selected operating modes, the quantity of liquid aspirated and dispensed from the laboratory pipette is governed by the calibration data signals stored in calibration memory 36. Trigger 46 is depressed and motor 16 is energized. Data signals corresponding to present piston 62 position are compared in micro-processor 24 with the calibration data signals. When the present position data signals or normalized calibration data signals, depending upon the quantity of liquid to be aspirated, equal the calibration data signals, motor 16 is deenergized and the quantity of liquid aspirated into the laboratory pipette is accurate because it considers that liquid specific temperature and density characteristic captured during the calibration procedure.

Keyboard 22 includes various control keys which govern the speed of motor 16. In the illustrated embodiment, by way of example, keyboard 22 contains 10 speed control buttons for regulating the speed of motor 16 which, in turn, governs the rate of aspirative and dispensing liquids. The ability of pipetting system 10 to pipette liquids at varying speeds is particularly useful as it relates to special applications. The slowest speeds, for example, allow the user to remove supernatent laying on top of cell monolayers without disturbing or resuspending the cells into solution. Conversely, the faster speeds are useful in applications where a powerful stream of liquid is aimed at a cell button that has been formed at the bottom of a test tube after centrifugation. This liquid stream is utilized to resuspend the cells into solution and is a delicate procedure that requires a powerful stream to resuspend the cells, yet one that will not lyse the cells rendering them unsuitable for further use.

In the illustrated embodiment, display 32 is provided with five indicating zones. Zone 1, the upper left section of the display, displays the current volume level of liquid in the pipette. Zone 2, the upper right section of the display, presents an indication of the pre-selected volumes for the (F) Fill and (D) Dispense modes as well as the current mode of operation of system 10. Zone 3, the lower left section of the display, is a message area which displays the mode of operation being performed, displays error messages, and provides operator instructions. Zone 4, the lower middle right section of the display, displays the cumulative volume of liquid which has been dispensed since last filled. Zone 5, the lower right section of the display, indicates which calibration channel is being used. The number 1 or 2 or 3 or 4 or 5 appears and denotes which one of the five channels is available to preset and store in memory the specific gravity and temperature of various liquids.

In a first automatic mode of operation, a single pull of trigger 46 will activate motor 16 and liquids will be aspirated or dispensed in the volumes programmed using keyboard 22 and displayed on display 32 in a calibration scheme according to the previously stored calibration data for the particular liquid. In a second automatic mode, trigger 46 is depressed throughout the pipetting step. If trigger 46 is released prior to completion of the pipetting step, display 32 and LED 92 or 94 provide an indication that the pipetting step has not been completed. The next time trigger 46 is depressed and held, the pipetting step is completed. This second automatic mode is unique in that it allows the user to be interrupted in the middle of a pipetting step and then continue with the pipetting step.

In a manual mode of operation, the programmed values are overridden and pipetting system 10 fills or dispenses as long as trigger 46 is depressed. The first trigger activation aspirates and subsequent trigger activations dispense until the pipette is empty.

Since certain changes may be made in the foregoing disclosure without departing from the scope of the invention herein involved, it is intended that all matter contained in the above description and depicted in the accompanying drawings be construed in an illustrative and not in a limiting sense.

What is claimed is:

1. A pipetting system comprising:
   (a) a hand held pipettor having pipette receptacle means and pump means;
   (b) pipette means including a calibration pipette and a laboratory pipette, said pipette means received in said pipette receptacle means;
   (c) drive means connected to said pump means, said drive means having first and second states, said pump means aspirating a liquid into said pipette means when said drive means is in said first state and dispensing a liquid from said pipette means when said drive means is in said second state;
   (d) means for generating a reference signal defining a selected quantity of liquid aspirated into said pump means;
   (e) memory means communicating with said generating means for storing said reference signal;
   (f) control means for energizing said drive means and actuating said pump means accordingly to said stored reference signal for aspirating a quantity of liquid into said laboratory pipette which is equal to said selected quantity;
   (g) pump means wherein said pump includes a piston which is constrained for reciprocating movement;
   (h) sensor means communicating with said pump means for sensing the position of said piston relative to a home position of said piston, the distance between said positions defining a quantity of liquid aspirated and dispensed by said pump means when in said first and second states;
   (i) display means communicating with said memory means for indicating the status of the pipetting system mode of operation;
   (j) indicator means mounted on said pipette, said indicator means communicating with said drive means for indicating the state of said drive means;
   (k) control means wherein said control means is separate from said pipettor, a cable connecting said control means and said pipettor; and
   (l) pipetting system wherein said indicator means is a pair of light emitting diode, said display means mounted on said control means.

2. A method for aspirating and dispensing a specific quantity of liquid comprising the steps of:
   (a) attaching a first calibration pipette to a pipettor, said first calibration pipette having means for indicating a selected quantity of liquid in said first calibration pipette;
   (b) energizing said pipettor and aspirating liquid into said first calibration pipette until said aspirated liquid is at said first calibration pipette indicating means;
   (c) storing data signals corresponding to the quantity of liquid aspirated into said first calibration pipette;
   (d) normalizing said first calibration data over the range of said pipettor capability of filing and dispensing a precise volume of liquid based on said first calibration data;
   (e) dispensing the liquid aspirated into said first calibration pipette;
   (f) removing said first calibration pipette and attaching a first laboratory pipette corresponding to said first calibration pipette corresponding to said first calibration pipette to said pipettor;
   (g) energizing said pipettor and aspirating a quantity of liquid corresponding to said stored first calibration data signals into said first laboratory pipette and further comprising
   (h) attaching a second calibrating pipette to said pipettor, said second calibration pipette to said pipettor, said second calibration pipette having means for indicating a selected quantity of liquid in said second calibration pipette;
   (i) energizing said pipettor and aspirating liquid into said second calibration pipette until said aspirated liquid is at said second calibration pipettor indicating means;
   (j) storing data signals corresponding to the quantity of liquid aspirated into said second calibration pipette in said memory means, said first calibration data and said second calibration data stored in separate channels in said memory means;
   (k) normalizing said second calibration data over the range of said pipettor capability of filing and dispensing a precise volume of liquid based on said second calibration data;
   (l) dispensing the liquid aspirated into said second calibration pipette;
   (m) removing said second calibration pipette and attaching a second laboratory pipette corresponding to said second calibration pipette to said pipettor; and
   (n) energizing said pipettor and aspirating a quantity of liquid corresponding to said stored second calibration data signals into said second laboratory pipette.

* * * * *